(12) United States Patent
Springer et al.

(10) Patent No.: US 6,423,856 B1
(45) Date of Patent: Jul. 23, 2002

(54) PROCESS FOR PREPARING ESTER PLASTICIZERS

(75) Inventors: Helmut Springer, Dinslaken; Klaus-Dieter Merscher, Buttelborn, both of (DE); Rudolf Heumuller, Repulse Bay Road (HK); Klaus Schimmer, Dossenheim; Heinz Strutz, Usingen, both of (DE)

(73) Assignee: Celanese Chemicals Europe GmbH (DE)

(*) Notice: Subject to any disclaimer, the term of this patent is extended or adjusted under 35 U.S.C. 154(b) by 6 days.

(21) Appl. No.: 09/644,913

(22) Filed: Aug. 24, 2000

(30) Foreign Application Priority Data

Aug. 28, 1999 (DE) .......................... 199 40 991

(51) Int. Cl.⁷ .................. C07C 51/00; C07C 69/00; C07C 67/02; C11C 1/00; C11C 3/00
(52) U.S. Cl. .................. 554/173; 560/129; 560/263
(58) Field of Search ................. 560/129, 263; 554/173

(56) References Cited

U.S. PATENT DOCUMENTS

| | | | | |
|---|---|---|---|---|
| 2,202,160 A | | 5/1940 | Marks | .................. 49/92 |
| 2,229,222 A | * | 1/1941 | Reid | .................. 260/488 |
| 2,340,482 A | | 2/1944 | Lycan | .................. 260/36 |
| 2,871,248 A | | 1/1959 | Kirkland et al. | .......... 260/410.6 |
| 4,297,262 A | * | 10/1981 | Phillips | .................. 260/31.6 |

FOREIGN PATENT DOCUMENTS

EP  0024722  3/1981

OTHER PUBLICATIONS

CRC Handbook of Chemistry and Physics, 54th edition. Robert C. Weast, editor. pp. D–6 and D–15 (1973).*
Ullmann's Encyclopedia of Industrial Chemistry, vol. 9, (5 pgs).
XP–002188592 (1 pg) 6001 Chem. Abstracts.
XP–002188628 (2 pgs).

* cited by examiner

Primary Examiner—Paul J. Killos
Assistant Examiner—Zachary Tucker
(74) Attorney, Agent, or Firm—Bierman, Muserlian and Lucas

(57) ABSTRACT

The present invention relates to a process for preparing ester plasticizers from ethylene glycol or the dimers, trimers or tetramers of this compound and linear or branched aliphatic monocarboxylic acids having from 3 to 20 carbon atoms. The reaction is carried out in the presence of organic substances having a boiling point of <112° C., in particular cyclohexane, as azeotrope formers (entrainers) for removing the water of reaction.

9 Claims, No Drawings

PROCESS FOR PREPARING ESTER PLASTICIZERS

The invention relates to a process for preparing ester plasticizers from ethylene glycol or the dimers, trimers or tetramers of this compound and linear or branched aliphatic monocarboxylic acids having from 3 to 20 carbon atoms in the presence of organic substances which have a boiling point of <112° C. and form azeotropes with water (hereinafter also referred to as azeotrope formers or entrainers) for removing the water of reaction.

Plasticizers are widely employed in many ways in plastics, coatings, sealants and rubber articles. They enter into a physical interaction with thermoplastic high polymers without reacting chemically, preferably by way of their solvent and swelling capabilities. This forms a homogeneous system whose thermoplastic range is shifted to lower temperatures compared to the original polymers, resulting in, inter alia, optimization of its mechanical properties, e.g. moldability, elasticity and strength are increased and the hardness is reduced.

For plasticizers to be suitable for a very wide range of applications, they have to meet a series of criteria. In the ideal case, they should be odorless, colorless and stable to light, cold and heat. In addition, it is expected that they should be insensitive to water, not be readily combustible and have a low volatility and not damage health. Furthermore, the preparation of the plasticizers should be simple and, in order to meet ecological requirements, should avoid the formation of waste materials such as by-products which cannot be utilized further and pollutant-containing wastewater.

Among the most important plasticizers are the esters of dicarboxylic and polycarboxylic acids with plasticizer alcohols, i.e. unbranched or branched primary alcohols having from about 6 to 20 carbon atoms, which are used as individual compounds or as mixtures. The esters are prepared, according to the classic method, by reacting the acids or acid anhydrides with an alcohol or a mixture of different alcohols in the presence of an acid, preferably sulfuric acid, as catalyst.

A specific class of ester plasticizers (referred to by the abbreviation G esters) comprises diols or ether diols, namely ethylene glycol, diethylene glycol, triethylene glycol and tetraethylene glycol, as alcohol component. They can be prepared in various ways. In addition to the reaction of alcohol and acid in the presence or absence of acid catalysts, further processes are employed in practice for obtaining G esters, for example the reaction of diol with acid halide, the transesterification of a carboxylic ester with a diol and the addition of ethylene oxide onto carboxylic acids (ethoxylation). In industrial manufacture, only the direct reaction of diol and carboxylic acid and the ethoxylation of carboxylic acids have become established as production processes, with the esterification of diol and acid being most preferred. This is because this process can be carried out readily in conventional chemical apparatuses and gives chemically uniform products. On the other hand, ethoxylation requires comprehensive and costly technical measures. Ethylene oxide is a very aggressive chemical substance. It can polymerize in an uncontrolled manner and forms explosive mixtures with air in a very wide range of mixing ratios. Ethylene oxide irritates the eyes and bronchial passages, leads to burns, to liver and kidney damage and is carcinogenic. Its handling therefore requires comprehensive safety measures. In addition, it is necessary for storage facilities and reaction apparatuses to be meticulously clean in order to avoid the formation of undesirable impurities due to secondary reactions of ethylene oxide with extraneous substances. Finally, the reaction with ethylene oxide is not very selective since it leads to mixtures of compounds having different chain lengths.

The direct esterification of alcohols with carboxylic acids is among the basic operations of organic chemistry. To increase the reaction rate, the reaction is usually carried out in the presence of catalysts. The use of one of the reactants in excess and/or the removal of the water formed during the reaction ensures that the equilibrium corresponding to the Law of Mass Action is shifted to the side of the reaction product, i.e. the ester, so that high yields are achieved.

Owing to the quality criteria for ester plasticizers described at the outset, the choice of catalyst and the procedure for removing the water of reaction are very important process features. This is because both these aspects of the process have a considerable influence on organoleptic and optical properties of the final products. The structure of the starting materials, viz. alcohol and acid, in turn has a critical effect on the mechanical and thermal properties of the plasticizers.

Although odor and color of the plasticizers can be matched to the desired requirements by addition of additives, the use of auxiliaries is to be avoided because they can impair other properties of the plasticizers and/or can limit their possible uses, e.g. because of incompatibility with the substrate.

Various methods of removing the water from the reaction formed from ethylene glycol (and its oligomers) and carboxylic acids in the esterification are known. Preference is given to azeotropic distillation in the presence of a water-immiscible solvent, heating the reaction mixture while passing an inert gas through it, and reacting the starting materials alcohol and carboxylic acid under reduced pressure or in the presence of a desiccant.

The removal of water by azeotropic distillation has proven to be particularly useful for adjusting the equilibrium in the preparation of ester plasticizers. However, the known methods and the entrainers used hitherto do not ensure that the high quality standards required for plasticizers are achieved.

It is therefore an object of the present invention to provide a process which makes it possible to prepare plasticizer esters based on ethylene glycol and oligomeric ethylene glycols in high purity and in high yields. In this context, it is particularly important that the process can be implemented using simple engineering means, that it ensures long operating times and that it gives consistently high-quality products over the entire operating time.

The invention provides a process for preparing ester plasticizers by reacting monoethylene, diethylene, triethylene or tetraethylene glycols with linear or branched aliphatic monocarboxylic acids having from 3 to 20 carbon atoms in the presence of an entrainer for removal of the water formed during the reaction as an azeotropic mixture. In the process of the present invention, organic substances having a boiling point of <112° C. are used as entrainers.

The new method is very reliable not only in laboratory and experimental operation, but also especially in industrial plants. It can be carried out easily, both batchwise and continuously, and gives plasticizers of high purity. A particularly notable aspect is the trouble-free and complete removal of the water of reaction and also of the entrainer used for removing the water. The complete removal of the reaction by-product and of the auxiliary results in the excellent color properties and the notable color stability of the ester plasticizers.

A critical feature of the process of the invention is the removal of the water of reaction from the reaction mixture and thus a displacement of the equilibrium in favor of the ester by means of organic substances whose boiling point is <112° C. The azeotrope formers are usually organic solvents which are available at a low price on an industrial scale. However, all other organic substances which have an appropriate boiling point and form azeotropes with water are also suitable. Examples of entrainers used according to the invention are hexane, 1-hexene, cyclohexane and toluene. Cyclohexane has been found to be a particularly advantageous azeotrope former. With water, cyclohexane forms a low-boiling binary system which can easily be distilled off from the mixture of reactants and product. The occurrence of binary or ternary mixtures with the reactants and with the ester is not observed. The removal of excess cyclohexane from the reaction mixture also presents no difficulties because of its low boiling point. The chemical stability and inertness of the cycloaliphatic hydrocarbon ensures that the reaction product is not contaminated by conversion products.

The amount of entrainer required for complete removal of the water can be determined in a simple manner from the water formation calculated according to the stoichiometry of the esterification reaction and from the composition of the binary azeotrope. It has been found useful to use the entrainer in excess, advantageously in an amount which is from 50 to 200% by weight above the theoretically calculated amount.

In a particularly useful embodiment of the process of the invention, the azeotrope former is added to the reaction mixture only after a temperature of at least 140° C., in particular from 150 to 170° C., has been reached and not before or during the heating procedure. This measure leads to particularly gentle and effective removal of the water. The entrainer can be added to the reaction mixture in portions or advantageously continuously at the rate at which it is consumed by azeotrope formation. The progress of the reaction can be followed in a simple manner by collection and separation of the entrainer/water mixture distilled off. The entrainer separated from the azeotrope can be returned directly, i.e. without an intermediate purification step, to the reaction.

The monoethylene, diethylene, triethylene and tetraethylene glycols used as starting materials for the process of the invention are industrially produced chemicals. The basic feedstock for their preparation is ethylene oxide from which (mono)ethylene glycol is obtained by heating with water under pressure. Diethylene glycol is obtained from ethylene glycol by ethoxylation. Triethylene glycol is obtained, like tetraethylene glycol, as by-product in the hydrolysis of ethylene oxide for preparing ethylene glycol. Both compounds can also be synthesized by reaction of ethylene glycol with ethylene oxide.

To obtain esters by the process of the invention, use is made of linear or branched, aliphatic monocarboxylic acids having from 3 to 20 carbon atoms in the molecule. Although saturated acids are preferred in many cases, unsaturated carboxylic acids can also be used as reaction components for the ester synthesis, depending on the application area for the plasticizers. Examples of carboxylic acids as building blocks of G esters are n-butyric acid, isobutyric acid, n-pentanoic acid, 2-methylbutyric acid, 3-methylbutyric acid, 2-methylpentanoic acid, 2-ethylbutyric acid, n-heptanoic acid, 2-methylhexanoic acid, cyclohexanecarboxylic acid, 2-ethylhexanoic acid, n-nonanoic acid, 2-methyloctanoic acid, isononanoic acid, 2-methylundecanoic acid, isoundecanecarboxylic acid, tricyclodecanecarboxylic acid and isotridecanecarboxylic acid. The novel process has been found to be particularly useful for preparing esters of the monoglycol or of the oligomeric glycols with $C_4$–$C_{13}$-monocarboxylic acids, preferably $C_5$–$C_9$-monocarboxylic acids.

The reaction of glycols and carboxylic acids can be carried out without use of a catalyst. This variant of the reaction has the advantage that it avoids introduction of extraneous substances into the reaction mixture which could lead to undesirable contamination of the ester. However, it is then generally necessary to maintain relatively high reaction temperatures because only this can ensure that the reaction proceeds at a sufficient, i.e. economically justifiable, rate. In this context, it should be noted that the increase in the temperature can lead to thermal damage to the ester. It is therefore not always possible to avoid use of a catalyst which aids the reaction and increases the reaction rate. The catalyst can frequently be an excess of the acid which is at the same time a reactant of the glycol. Otherwise, the usual esterification catalysts are suitable for influencing the reaction rate, for example sulfuric acid, formic acid, polyphosphoric acid, methanesulfonic acid or p-toluenesulfonic acid and likewise combinations of such acids. Preference is given to using catalytically active compounds which are solid under the reaction conditions and are insoluble in the reaction system, for example alkali metal or alkaline earth metal hydrogensulfate, in particular sodium hydrogensulfate,;since these can be removed from the reaction mixture by simple filtration after the esterification is complete and no additional treatment of the reaction mixture is necessary afterwards. The amount of catalyst used can extend over a wide range. It is possible to use both 0.01% by weight and 5% by weight of catalyst, based on the reaction mixture. However, since relatively large amounts of catalyst bring few advantages, the catalyst concentration is usually from 0.01 to 1.0% by weight, preferably from 0.01 to 0.5% by weight, in each case based on the reaction mixture. It may be advantageous to decide on the basis of preliminary experiments for each individual case whether the reaction should be carried out without catalyst at relatively high temperature of with catalyst at lower temperature.

The esterification can be carried out using stoichiometric amounts of alcohol and acid. However, the diol is preferably allowed to react with excess acid in order to achieve very complete conversion in a finite time.

Depending on the starting materials, the reaction between alcohol and acid commences in the range from about 150 to 170° C. It can be brought to completion at temperatures up to about 250° C. These cited temperatures are guideline values to which it is useful to adhere. Lower temperatures may, for example, be sufficient when a sufficiently high reaction rate is achieved in the specific case or only partial conversions are sought. Higher temperatures are possible if the occurrence of decomposition products which, for example, cause discoloration is to be ruled out. The use of subatmospheric or superatmospheric pressure is not ruled out, but it will be restricted to special cases.

The reaction mixture obtained after the reaction is complete may comprise not only the ester as desired reaction product but also unreacted starting materials, in particular excess acid (if an excess of acid has been employed). For the work-up, the reaction mixture is freed of catalyst by conventional methods. If the catalyst is present as a solid, e.g. in the form of a hydrogensulfate, the product is filtered in customary filtration apparatuses at room temperature or at temperatures up to 150° C. The filtration can be assisted by customary filter aids such as cellulose, silica gel, kieselguhr or wood flour. Excess and unreacted starting materials are subsequently distilled off. In order to remove the last residues of acidic constituents, a further treatment with an alkaline reagent, e.g. aqueous sodium carbonate or sodium hydroxide solution, can be provided. After phase separation, the ester is dried by, for example, passing an inert gas through the product or applying a vacuum. If the catalyst is dissolved in the reaction mixture, for example sulfuric acid or p-toluenesulfonic acid, any remaining starting materials are first distilled off, if desired after prior filtration, and the product is then treated with an alkaline reagent and dried.

If required by the envisaged application, the isolation of the ester can be followed by further purification steps, for example distillation under reduced pressure.

A series of diesters of monoethylene, diethylene, triethylene and tetraethylene glycol have been prepared by the novel process. Specifically, these are the diesters of monoethylene glycol with one of the following carboxylic acids: 3-methylbutyric acid, 2-methylhexanoic acid, 2-methyloctanoic acid, 3,5,5-trimethylhexanoic acid, particularly in the form of isononanoic acid, an industrial product in which about 95% by weight of 3,3,3-trimethylhexanoic acid is present, 2-methylundecanoic acid; the diesters of diethylene glycol with one of the following carboxylic acids: 2-methylbutyric acid, 3-methylbutyric acid, 2-methyloctanoic acid, 2-methylundecanoic acid; the diesters of triethylene glycol with one of the following carboxylic acids: 2-methylbutyric acid, 2-methylhexanoic acid, cyclohexanecarboxylic acid, 2-methyloctanoic acid, 3,5,5-trimethylhexanoic acid, particularly in the form of isononanoic acid, an industrial product in which about 95% by weight of 3,5,5-trimethylhexanoic acid is present, 2-methylundecanoic acid; finally the diesters of tetraethylene glycol with one of the following carboxylic acids: isobutyric acid, n-pentanoic acid, 2-methylbutyric acid, 3-methylbutyric acid, n-hexanoic acid, 2-methylpentanoic acid, 2-methylhexanoic acid, cyclohexanecarboxylic acid, 2-methyloctanoic acid, 3,5,5-trimethylhexanoic acid, particularly in the form of isononanoic acid, an industrial product in which about 95% by weight of 3,5,5-trimethylhexanoic acid is present, and 2-methylundecanoic acid.

The esters of ethylene glycol and of its oligomers are very useful as plasticizers for all customary thermoplastic high polymers. They have been found to be particularly useful as additives to polyvinyl butyral, which is used in admixture with glycol esters as intermediate layer for producing multilayer or laminated glass.

The process of the invention can be carried out batchwise or continuously in the reaction apparatuses typical of chemical industry. Stirred vessels provided with a heating facility and a device for introducing the azeotrope former, e.g. an immersed tube, have been found to be useful.

The following examples illustrate the process of the invention, but do not restrict it to the embodiments described.

EXAMPLE 1

Preparation of Tetraethylene Glycol Di-3-methylbutyrate

The esterification of tetraethylene glycol with 3-methylbutyric acid is carried out in a heatable 2 l four-necked flask which is fitted with a stirrer, internal thermometer and immersed tube and is connected via a distillation attachment to a 1 l receiver with a bottom outlet. The receiver is provided with an immersed tube which is connected by means of tubing via a pump to the immersed tube of the reaction flask.

582.6 g of tetraethylene glycol, 766.2 g of 3-methylbutyric acid and 4.1 g of potassium hydrogensulfate are placed in the flask and heated while stirring to 180° C. After reaching an internal temperature of 160° C., 700 ml/h of cyclohexane are pumped from the receiver via the immersed tube into the flask. The cyclohexane/water azeotrope which distills off at the same time is collected and separated in the receiver. The upper phase consisting predominantly of cyclohexane together with small amounts of carboxylic acid is recirculated to the reactor.

The course of the reaction is followed by continuous weighing of the water obtained in the receiver and by sampling and gas-chromatographic analysis of the samples. The following table shows the results of the gas-chromatographic analysis:

|  | 1 h | 2 h | 3 h | 5 h | 10 h |
| --- | --- | --- | --- | --- | --- |
| Cyclohexane | 4.5% | 2.9% | 2.6% | 4.4% | 5.9% |
| 3-Methylbutyric acid | 48.0% | 37.1% | 24.8% | 10.8% | 9.5% |
| Tetraethylene glycol | 14.7% | 10.4% | 5.9% | 0.2% |  |
| Monoester | 22.5% | 30.7% | 32.1% | 8.2% | 0.5% |
| Diester | 6.5% | 17.0% | 32.1% | 71.2% | 75.5% |
| Others | 3.8% | 1.9% | 2.5% | 5.2% | 8.6% |

The crude ester obtained after conclusion of the esterification (1189.9 g) is freed of the catalyst by simple filtration and is purified by distillation; the boiling point is 189° C./1 mbar. Tetraethylene glycol di-3-methylbutyrate has a density of 1.020 g/cm$^3$ at 20° C. and a solidification temperature of <−30° C.; at 20° C., the diester has a viscosity of 16.8 mPa·s.

EXAMPLE 2

Preparation of Tetraethylene Glycol Diisononanoate

Using a method analogous to the ester synthesis described in Example 1, 388.4 g of tetraethylene glycol and 791.2 g of isononanoic acid are reacted in the presence of 2.8 g of potassium hydrogensulfate. After a reaction time of 10 hours at 180° C., 1127.7 g of crude ester having the following composition are obtained:

| Cyclohexane | 5.9% |
| --- | --- |
| Isononanoic acid | 12.5% |
| Tetraethylene glycol | — |
| Monoester | 0.1% |
| Diester | 77.4% |
| Others | 4.1% |

The catalyst is separated off by simple filtration and the ester is purified by distillation; the boiling point of tetraethylene glycol diisononanoate is 219° C./1 mbar.

EXAMPLE 3

Preparation of Tetraethylene Glycol Di-2-methylbutyrate

Using a method analogous to the ester synthesis described in Example 1, 582.6 g of tetraethylene glycol and 766.0 g of 2-methylbutyric acid are reacted in the presence of 4.1 g of potassium hydrogensulfate. After a reaction time of 10 hours at 180° C., 1200.4 g of crude ester having the following composition are obtained:

| | |
|---|---|
| Cyclohexane | 6.4% |
| 2-Methylbutyric acid | 10.2% |
| Tetraethylene glycol | — |
| Monoester | 0.8% |
| Diester | 75.2% |
| Others | 7.4% |

The catalyst is separated off by simple filtration and the ester is purified by distillation; the boiling point is 186° C./1 mbar. Tetraethylene glycol di-2-methylbutyrate has a density of 1.022 g/cm$^3$ at 20° C. and a solidification temperature of <−30° C.; at 20° C., the diester has a viscosity of 12.7 mPa·s.

EXAMPLE 4

Preparation of Tetraethylene Glycol Di-n-pentanoate

Using a method analogous to the ester synthesis described in Example 1, 582.6 g of tetraethylene glycol and 766.0 g of n-pentanoic acid are reacted in the presence of 4.1 g of potassium hydrogensulfate. After a reaction time of 5 hours at 180° C., 1225.2 g of crude ester having the following composition are obtained:

| | |
|---|---|
| Cyclohexane | 7.2% |
| n-Pentanoic acid | 10.2% |
| Tetraethylene glycol | — |
| Monoester | 0.2% |
| Diester | 76.7% |
| Others | 5.7% |

The catalyst is separated off by simple filtration and the ester is purified by distillation; the boiling point is 196° C./1 mbar. Tetraethylene glycol di-n-pentanoate has a density of 1.026 g/cm$^3$ at 20° C. and a solidification temperature of −42° C.; at 20° C., the diester has a viscosity of 14.0 mPa·s.

EXAMPLE 5

Preparation of Tetraethylene Glycol Diisobutyrate

Using a method analogous to the ester synthesis described in Example 1, 621.4 g of tetraethylene glycol and 704.8 g of isobutyric acid are reacted in the presence of 4.4 g of potassium hydrogensulfate. After a reaction time of 10 hours at 180° C., 1201.0 g of crude ester having the following composition are obtained:

| | |
|---|---|
| Cyclohexane | 12.2% |
| Isobutyric acid | 11.3% |
| Tetraethylene glycol | — |
| Monoester | 2.3% |
| Diester | 71.3% |
| Others | 2.9% |

The catalyst is separated off by simple filtration and the ester is purified by distillation; the boiling point is 171° C./1.4 mbar.

EXAMPLE 6

Preparation of Triethylene Glycol Diisononanoate

Using a method analogous to the ester synthesis described in Example 1, 375.5 g of triethylene glycol and 988.8 g of isononanoic acid are reacted in the presence of 3.4 g of potassium hydrogensulfate. After a reaction time of 6 hours at 180° C., 1281.6 g of crude ester having the following composition are obtained:

| | |
|---|---|
| Cyclohexane | 6.4% |
| Isononanoic acid | 17.5% |
| Triethylene glycol | — |
| Monoester | — |
| Diester | 69.4% |
| Others | 6.7% |

The catalyst is separated off by simple filtration and the ester is purified by distillation; the boiling point is 220° C./0.8 mbar.

EXAMPLE 7

Preparation of Tetraethylene Glycol Di-n-hexanoate

Using a method analogous to the ester synthesis described in Example 1, 485.5 g of tetraethylene glycol and 726.3 g of n-hexanoic acid are reacted in the presence of 3.4 g of potassium hydrogensulfate. After a reaction time of 5 hours at 180° C., 1122.1 g of crude ester having the following composition are obtained:

| | |
|---|---|
| Cyclohexane | 7.4% |
| n-Hexanoic acid | 12.4% |
| Tetraethylene glycol | — |
| Monoester | 0.5% |
| Diester | 75.9% |
| Others | 3.8% |

The catalyst is separated off by simple filtration and the ester is purified by distillation; the boiling point is 205° C./0.7 mbar.

EXAMPLE 8

Preparation of Triethylene Glycol Di-2-methylbutyrate

Using a method analogous to the ester synthesis described in Example 1, 450.6 g of triethylene glycol and 766.0 g of 2-methylbutyric acid are reacted in the presence of 4.1 g of potassium hydrogensulfate. After a reaction time of 9 hours at 180° C., 1057.0 g of crude ester having the following composition are obtained:

| | |
|---|---|
| Cyclohexane | 6.1% |
| 2-Methylbutyric acid | 9.3% |
| Triethylene glycol | — |
| Monoester | 0.1% |
| Diester | 77.7% |
| Others | 6.8% |

The catalyst is separated off by simple filtration and the ester is purified by distillation; the boiling point is 150° C./1 mbar.

EXAMPLE 9

Preparation of Tetraethylene Glycol Di-cyclohexane-carboxylate

Using a method analogous to the ester synthesis described in Example 1, 485.5 g of tetraethylene glycol and 801.3 g of cyclohexanecarboxylic acid are reacted in the presence of 3.4 g of potassium hydrogensulfate. After a reaction time of 5 hours at 180° C., 1215.7 g of crude ester having the following composition are obtained:

| | |
|---|---|
| Cyclohexane | 4.1% |
| Cyclohexanecarboxylic acid | 11.3% |
| Tetraethylene glycol | — |
| Monoester | 0.3% |
| Diester | 79.3% |
| Others | 5.0% |

The catalyst is separated off by simple filtration and the ester is purified by distillation.

EXAMPLE 10

Preparation of Triethylene Glycol Dicyclohexane-carboxylate

Using a method analogous to the ester synthesis described in Example 1, 375.5 g of triethylene glycol and 801.3 g of cyclohexanecarboxylic acid are reacted in the presence of 3.4 g of potassium hydrogensulfate. After a reaction time of 7 hours at 180° C., 1080.3 g of crude ester having the following composition are obtained:

| | |
|---|---|
| Cyclohexane | 4.6% |
| Cyclohexanecarboxylic acid | 11.5% |
| Triethylene glycol | — |
| Monoester | 0.1% |
| Diester | 78.4% |
| Others | 1.9% |

The catalyst is separated off by simple filtration and the ester is purified by distillation.

EXAMPLE 11

Preparation of Tetraethylene Glycol Di-2-methylhexanoate

Using a method analogous to the ester synthesis described in Example 1, 485.5 g of tetraethylene glycol and 813.8 g of 2-methylhexanoic acid are reacted in the presence of 3.4 g of potassium hydrogensulfate. After a reaction time of 10 hours at 180° C., 1209.7 g of crude ester having the following composition are obtained:

| | |
|---|---|
| Cyclohexane | 5.9% |
| 2-Methylhexanoic acid | 12.9% |
| Tetraethylene glycol | — |
| Monoester | 0.1% |
| Diester | 73.9% |
| Others | 7.2% |

The catalyst is separated off by simple filtration and the ester is purified by distillation.

EXAMPLE 12

Preparation of Diethylene Glycol Di-3-methylbutyrate

Using a method analogous to the ester synthesis described in Example 1, 371.4 g of diethylene glycol and 893.4 g of 3-methylbutyric acid are reacted in the presence of 4.8 g of potassium hydrogensulfate. After a reaction time of 10 hours at 180° C., 1039.3 g of crude ester having the following composition are obtained:

| | |
|---|---|
| Cyclohexane | 5.2% |
| 3-Methylbutyric acid | 12.7% |
| Diethylene glycol | — |
| Monoester | 2.2% |
| Diester | 78.8% |
| Others | 1.1% |

The catalyst is separated off by simple filtration and the ester is purified by distillation.

What is claimed is:

1. A process for preparing ester plasticizers by reacting monoethylene, diethylene, triethylene or tetraethylene glycols with linear or branched aliphatic monocarboxylic acids having from 3 to 20 carbon atoms in the presence of an entrainer for removal of the water formed during the reaction as an azeotropic mixture, wherein the entrainer used is an organic substance having a boiling point of <112° C. and wherein the entrainer is added to the reaction mixture after a temperature of at least 140° C. has been reached.

2. The process as claimed in claim 1, wherein the entrainer used is cyclohexane.

3. The process as claimed in claim 1 wherein the entrainer is added to the reaction mixture after a temperature of from 150 to 177° C. has been reached.

4. The process as claimed in claim 1, wherein the entrainer is added to the reaction mixture in a plurality of portions.

5. The process as claimed in claim 3, wherein the entrainer is added continuously to the reaction mixture.

6. The process as claimed in claim 1, wherein the monocarboxylic acid is used in a stoichiometric excess of from 0.05 to 1.5 mol per mole of monethylene, diethylene, triethylene or tetraethylene glycol.

7. The process as claimed in claim 1, wherein the reaction is carried out in the presence of an alkali metal hydrogensulfate or alkaline earth metal hydrogensulfate as catalyst.

8. The process as claimed in claim 1 wherein the reaction is conducted in the presence of a catalyst in an amount of from 0.01 to 1.0% by weight, based on the reaction mixture.

9. The process as claimed in claim 1, wherein the reaction is carried out at temperatures of from 150 to 250° C.

\* \* \* \* \*